(12) United States Patent
Hochgraeber et al.

(10) Patent No.: US 9,778,278 B2
(45) Date of Patent: Oct. 3, 2017

(54) SAMPLE-TAKING UNIT

(71) Applicant: DIONEX SOFTRON GMBH, Germering (DE)

(72) Inventors: Hermann Hochgraeber, Offenberg (DE); Robert Springer, Germering (DE)

(73) Assignee: DIONEX SOFTRON GMBH, Germering (DE)

( * ) Notice: Subject to any disclaimer, the term of this patent is extended or adjusted under 35 U.S.C. 154(b) by 125 days.

(21) Appl. No.: 14/792,038

(22) Filed: Jul. 6, 2015

(65) Prior Publication Data
US 2016/0011082 A1    Jan. 14, 2016

(30) Foreign Application Priority Data
Jul. 9, 2014   (DE) ........................ 10 2014 109 631

(51) Int. Cl.
*G01N 35/10* (2006.01)
*B01L 3/00* (2006.01)
*G01N 30/18* (2006.01)

(52) U.S. Cl.
CPC ...... *G01N 35/1079* (2013.01); *B01L 3/50825* (2013.01); *G01N 30/18* (2013.01)

(58) Field of Classification Search
CPC ........... G01N 35/1079; G01N 35/00–35/1097; G01N 2035/00019–2035/1076

USPC ........................................... 73/64.56, 863.85
See application file for complete search history.

(56) References Cited

U.S. PATENT DOCUMENTS

| | | | |
|---|---|---|---|
| 2005/0074363 A1* | 4/2005 | Dunfee | G01N 35/1004 422/81 |
| 2009/0044607 A1 | 2/2009 | Hochgraeber et al. | |
| 2011/0120237 A1 | 5/2011 | Leroi et al. | |
| 2013/0322200 A1 | 12/2013 | Ludwig | |

FOREIGN PATENT DOCUMENTS

| | | |
|---|---|---|
| DE | 102006007542 | 9/2007 |
| DE | 102008023051 | 11/2009 |
| DE | 102012104708 | 7/2013 |

* cited by examiner

*Primary Examiner* — Peter Macchiarolo
*Assistant Examiner* — Nathaniel Kolb
(74) *Attorney, Agent, or Firm* — Timothy J. Ohara

(57) ABSTRACT

A sample-taking unit having a sampling unit and a hold-down device which is movable relative thereto in a parallel manner, said sample-taking unit including a self-holding mechanism which, as a result of a self-locking effect, automatically fixes the hold-down device in a lowered fixing position against an upward movement until the self-locking effect is removed again as a result of the self-holding mechanism being acted upon with a detaching force, preferably as a result of contact between the sampling unit and a clamping element of the self-holding mechanism.

21 Claims, 3 Drawing Sheets

SAMPLE-TAKING UNIT

CROSS REFERENCE TO RELATED APPLICATIONS

This application is claims the priority benefit under 35 U.S.C. §119 to German Patent Application No. 10 2014 109 631.2, filed on Jul. 9, 2014, the disclosure of which is incorporated herein by reference.

FIELD OF THE INVENTION

The invention relates to a sample-taking unit that is used in particular in the field of high pressure liquid chromatography (HPLC).

BACKGROUND

In HPLC samples are kept in containers (small bottles or microtiter plates) which are frequently sealed by so-called septa. To take a sample, a penetrating element is jabbed through the septa in order to be able to take up the sample through the hollow needle. On the one hand the penetrating element can be a sample needle, by means of which the sample is directly taken up, the needle piercing and contacting the septum. However, synonymous with the invention, the penetrating element can also be a so-called pricker which, in the form of a needle with a larger inside diameter, penetrates the septum and comprises in its interior a free channel for the friction-free passage of a sample needle. The pricker prepares the path for the sample needle into the container as it were and protects it against contact with the septum or in general the container covering. Whilst in this case it is possible to withdraw the needle itself in a friction-free manner out of the container, the pricker rubs against the septum. A moving unit moves the pricker up and down and carries a further moving unit which can move or at least guide the sample needle relative to the pricker.

When the penetrating element is subsequently withdrawn from the container it must be ensured that the container is held in its position in spite of the friction forces between the penetrating element and the septum. Otherwise it would be conceivable for a penetrating element, which is to be withdrawn upward from the container, also to raise the container by means of the friction forces, which could result in collisions between the sample vessel and other vessels or devices of the sampler.

In order to avoid this, the prior art makes known hold-down devices which act upon the top surface of the container or of the septum with a holding force whilst the penetrating element is pulled out. The hold-down device can be moved up and down by means of an own drive where applicable. As an alternative to this, a sprung coupling with the sampling unit which moves the penetrating element is also known. In this case, the hold-down device is pressed onto the container at an increasing spring force whilst the penetrating element penetrates the septum. When the movement of the sampling unit is in the opposite direction, the spring force must be great enough to enable the penetrating element to be pulled out of the container completely before the spring force weakens too much and the hold-down device together with the sampling unit is able to move upwards again.

As an alternative to this, cascaded drives are also known where the drive of the sampling unit is moved together with the hold-down device by means of a hold-down device drive. As soon as the hold-down device is placed in position and consequently fixes the sample vessel, the drive is actuated in order to move the penetrating element into the container and then out again. The hold-down device can then be raised from the vessel together with the sampling unit it is carrying.

The aforementioned structures are expensive and the requirements are only unsatisfactorily met. Cascaded drives require increased expenditure on structure and control. In the case of the spring-preloaded hold-down devices, to pierce the penetrating element the spring force always has to be countered, which loads the drives unnecessarily. In addition, the spring force changes in dependence on the depth of insertion of the needle or of the pricker. As a rule, very long compression or tension springs are used for a hold-down force that is as uniform as possible, which requires increased installation space. In addition, such compression springs can buckle or scrape against their guides.

SUMMARY

Consequently, it has been the object of the invention to provide a hold-down device for sample vessels which can provide a hold-down force that is always sufficient with the smallest expenditure on structures.

The invention is based on the knowledge that it is possible to generate a hold-down force that is always sufficient in a particularly simple manner by utilizing the principle of self-locking such that, irrespective of the depth of insertion of the penetrating element or of the different friction forces between the penetrating element and the septum, a sufficient holding force can always be ensured at minimum structural expense. To this end, the hold-down device is held by means of a self-locking mechanism in a fixing position, in which it is to act upon the container with a holding force and consequently fix it, whilst the sampling unit pulls the penetrating elements or preferably element out of the vessel. The self-locking acts in the manner of a freewheel which allows the downward movement of the hold-down device in the direction of the container ("freewheel direction"), but blocks or prevents its movement in the opposite direction ("blocking direction") as a result of frictional and/or positive locking. Said self-locking effect is maintained by means of a self-holding mechanism according to the invention until a detaching force which acts on the mechanism eliminates the self-locking effect, as a result of which the hold-down device is able to leave its fixing position and can be raised from the vessel. "Self-locking" in the sense of the present invention is also to include the case where a relative movement is prevented as a result of positive locking, for instance as a result of interlocking latching elements along a sawtooth-like profile rail, among other things. It is to be characterized by an increased force in the blocking direction not being able to overcome the self-locking effect, but resulting instead in an increased counter force.

In relation to the prior art such a sample-taking unit is distinguished by particularly simple structural means (the self-holding mechanism can be formed by two simple, interacting molded parts), at the same time a holding force that is always sufficient being ensured in a reliable manner. The holding force mainly depends directly on the friction force between the penetrating element and the septum and at an extensively constant friction force is also "automatically" constant. Spring forces which vary along a stroke path are no longer an issue.

The sample-taking unit according to the invention then includes a sampling unit with a penetrating element. To take a sample from the container, the penetrating element is movable from a first, preferably top end position into a second, preferably bottom end position in which it projects through the top surface of the container or projects into the container. The second end position, depending on the design of the penetrating element as a pricker or sample needle, is chosen at a pre-definable depth in the container. The sampling unit is movable from said second end position in the direction of a first end position, it also being able to assume a detaching position (explained in more detail below). In the detaching position or the first end position, the penetrating element is uncoupled from the container such that there is no friction locking connection between it and the container or a septum covering the container. The detaching position, in which the self-locking effect is eliminated, can at the same time correspond to the second or top end position of the sampling unit, for example when the hold-down device described below is moved upward again independently once the self-locking effect has been eliminated and further raising of the sampling unit is not necessary.

In addition, the sample-taking unit according to the invention includes a hold-down device which is movable relative to the penetrating element. The hold-down device is movable from a fixing position, in which it fixes the container, into a release position, in which it does not act upon the container. In this case, it is provided that the hold-down device maintains the fixing position by means of a holding mechanism whilst the sampling unit is moved from the second end position in the direction of the first end position. This ensures that the penetrating element is able to be pulled upward completely out of the septum which covers the container whilst the holding mechanism still acts upon the container or the septum and thus fixes any unwanted movement.

The sample-taking unit according to the invention is characterized in that the holding mechanism is realized as a self-holding mechanism, by means of which the hold-down device can be fixed in the fixing position as a result of a self-locking effect with a clamping force. In contrast to the prior art, where the hold-down device is pressed onto the container either by a spring force or by means of an independent drive, the sample-taking unit according to the invention manages without any such additional means. Instead, the self-holding mechanism acts on the hold-down device such that said hold-down device is able to perform a movement in the direction of the container ("freewheel direction") whilst it is automatically blocked against a movement in the opposite direction ("blocking direction") by means of the self-holding mechanism. This is realized in detail as a result of individual components of the self-holding mechanism interacting with one another in such a manner that a relative movement of the components with respect to one another in the freewheel direction (when the hold-down device is moved in the direction of the container) is subject to an at best slight and easily surmountable sliding friction, whilst the components in the case of a relative movement attempted in the blocking direction interact in a frictionally-locking or positive-locking manner and block the relative movement.

A simple example of said operating principle is known for a conventional screw clamp where a clamping arm which carries the actual screw spindle engages around a clamping body which is realized as a rail and when acted upon with a clamping force tilts on the rail. Even an increasing clamping force does not result in removing said self-locking effect as long as the force ratios and friction angle known to the expert for the phenomenon of self-locking are maintained. The self-locking effect is not eliminated until a detaching force, which counters the clamping force and eliminates it, is applied to the clamping arm such that the clamping arm is able to be moved freely along the clamping arm.

The self-locking effect of the retaining mechanism according to the invention is initially maintained independently of the position of the sampling unit or of the penetrating element. High or increasing friction forces between the septum and the penetrating element that is pulled out of said septum always generate a corresponding counter force which holds the hold-down device securely in the fixing position on account of the self-locking effect. In contrast, in the prior art a sufficiently highly dimensioned spring force has always to be ensured for pressing down the hold-down device relative to the sampling unit. Such a spring can be omitted entirely according to the invention and the reliably functioning self-holding mechanism can be realized in an installation space that is clearly smaller than is possible using the known and often elongated compression springs.

The self-holding mechanism preferably comprises a clamping element and a clamping body, wherein the self-locking is to be active and the clamping force which holds the hold-down device in its fixing position is consequently to be transmitted between the two. The clamping body is preferably realized as a clamping rail, the clamping element sliding past the clamping rail without interacting in a self-locking manner with the rail when the two elements are moved relative to one another in the freewheel direction. A reverse movement, in contrast, results in the clamping element being tensioned, tilted or clamped on or against the clamping rail, which makes the relative movement in said direction impossible.

In an expedient manner the clamping element is spring-preloaded in order to exclude hysteresis between it and the clamping rail. As a result of the spring preloading, the clamping element always abuts directly against the clamping rail in order to generate a self-locking effect immediately when the movement is reversed (for a screw clamp this corresponds to when the clamping arm assumes the position which is tilted on the clamping rail and inclined slightly downward). In said alignment it can be displaced upward in the direction of the top clamping lever in the region of the clamping rail, that is in the freewheel direction. If an attempt is made to reverse said relative movement—if a lifting force is exerted by the container onto the hold-down device—the self-locking effect, which fixes the hold-down device securely in its position, is generated immediately and without play between the spring-loaded clamping element and the clamping rail on account of the direct contact already established between both components.

In the same way such preloading can also be generated by applying gravitational force instead of spring preloading. A lever which is always pressed down by its weight into a "fixing position" would at all times assume the alignment in which, on movement reversal, it could immediately interact and tilt in a clamping manner with the clamping rail.

It can be provided for sample taking according to the invention that either the clamping body is fixed in position and the clamping element is movable together with the hold-down device or the clamping element is fixed in position and the clamping body is movable together with the hold-down device. The crucial factor is the interaction between the two components with respect to one another, for which it is basically insignificant whether the clamping body or the clamping element is moved together with the hold-down device. It is characteristic of the self-locking mechanism according to the invention that the clamping element and the clamping body abut against one another or slide past one another in a first relative movement in relation to one another, that is in the freewheel direction, without building up forces which block the movement. When an attempt is made to change the direction of movement into the opposite direction, the clamping element and clamping body, in contrast, lock in or on one another such that the movement is prevented on account of the clamping forces which are generated as a result of the self-locking effect.

In order, where required, to be able to remove the generated self-locking effect which holds the hold-down device in its fixing position, two variants are of particular interest. The self-locking effect is removed by generating a detaching force which cooperates with the self-locking mechanism, in particular with the clamping element.

a) Said detaching force can be introduced by the sampling unit by said sampling unit, in a relative movement in relation to the hold-down device, acting upon the clamping element (preferably by means of an entrainment means provided especially for this purpose) such that the detaching force introduced into the clamping element acts counter to the clamping force resulting from the self-locking effect and overcomes the same such that the self-locking effect is eliminated. For the case of the uprightly arranged clamping screw with a bottom clamping lever which is tensioned against the upper clamping lever by means of self-locking, this would mean that a detaching force would be introduced from above in the region of the clamping rail on its side remote from the clamping element onto the bottom clamping lever which would cancel the tilting of the clamping lever with the clamping rail. Such an embodiment ensures, in a manner that is particularly technically elegant, the automatic elimination of the self-locking effect by the sampling unit, which is raised upward by the container, precisely at the moment at which the penetrating element has been completely pulled out from the container or the septum. By suitably choosing the geometric dimensions of the hold-down device, of the self-locking mechanism, of the sampling unit and of the paths of movement of the hold-down device and of the sampling unit, it can then be ensured very simply that the self-locking effect is eliminated in a targeted manner at the suitable moment by means of a component of the sample-taking unit that is present in any case, namely the sampling unit which moves away from the container.

b) As an alternative to this, it is possible, by means of an actuatable actuator, to introduce into the clamping element a detaching force which is drivable in a pneumatic, electromagnetic, hydraulic or other manner. In this way, the triggering of the self-locking effect can be actuated at a suitable arbitrary moment irrespective of the position of the sampling unit, however at the cost of the additionally necessary actuator.

Although the detaching force for eliminating the self-locking effect is preferably to be introduced into the clamping element, it is fundamentally also possible to act upon the clamping body instead, also in the form of a clamping rail, with the detaching force. To this end, the clamping rail could be pivoted or translationally deflected, for example, in order to cancel the force coupling to the clamping element. In an expedient manner the clamping body is a straight, elongated element (rail, guide, rod etc.) with a correspondingly straight contact surface which can interact with the clamping element. The clamping body can be arranged fixed in position and can serve as a guide of the hold-down device which is movable relative thereto, the clamping element then being moved together with the hold-down device. Conversely, the hold-down device can also be moved up and down together with such a clamping body whilst its elongated contact surface can slide along a clamping element which is arranged in a fixed position or can develop a clamping action with said clamping element.

According to a preferred embodiment of the invention, the hold-down device is movable by means of the sampling unit from the release position into the fixing position and/or into the opposite direction. The advantage of this is that the movement of the hold-down device does not have to be provided by a separate drive, this can occur instead by being acted upon with the sampling unit. As a result, the hold-down device can be moved downward initially together with the sampling unit in the direction of the container until the hold-down device rests on the top surface of the container or the septum. The hold-down device, in this case, is able to be moved just as a result of its weight or by being acted upon by the sampling unit. During said downward movement of the hold-down device, the self-holding mechanism, which is coupled to said hold-down device, is actuated in the freewheel direction in which the relative movement between the clamping body and the clamping element is not blocked.

A relative movement permitted between the hold-down device and the sampling unit then allows the sampling unit to move further down with the penetrating element projecting downward in order to penetrate through the septum with the penetrating element. The hold-down device remains fixed in position during this time. After removing the sample from the container, the sampling unit is raised upward again in the opposite direction. In this case, upwardly directed forces acting from the penetrating element onto the septum and consequently onto the hold-down device are compensated according to the invention by the self-locking effect which starts to act at the moment said lifting force is introduced by means of the hold-down device into the self-holding mechanism which is operated in the "blocking direction" in the case of an attempted upward movement of the hold-down device, therefore directly blocking said movement.

The sampling unit, on the other hand, can be moved further upward until the penetrating element has been completely pulled out of the container and lasting fixing of the container is no longer necessary. In the further upward movement of the sampling unit, said sampling unit can consequently, according to the invention, act upon the hold-down device from below with a lifting force in order to raise it from the container. This can only occur once the self-locking effect, initially still existing, has been eliminated. This can occur in turn as a result of the abovementioned variants, according to which either the sampling unit itself (where applicable by means of an entrainment means) exerts a detaching force onto the clamping element (or the clamping body), or by a separately actuatable actuator acting on the self-holding mechanism in order to eliminate the self-locking effect. The desired upward movement of the hold-down device is then no longer blocked such that the upward moving sampling unit is able to raise the hold-down device with it and move it upward in order to release the container completely. This is explained once again by way of the representations of the figures.

According to an advantageous embodiment of the invention, the hold-down device is movable into the fixing position against a spring force. For example, in the case of the afore-described downward movement of the sampling unit, by generating a spring force the hold-down device could be pushed down into the fixing position where it is initially fixed by way of the already-described self-holding mechanism against a backward movement. The spring force therefore acts in the blocking direction. When the sampling unit moves upward after successfully taking a sample and after the self-holding mechanism has been removed by means of being acted upon by the sampling unit or its entrainment means, the hold-down device, due to the spring force, can be moved upward directly into its release position without the sampling unit having had to raise it to there. This results in the advantage that, once the self-locking effect has been removed, the hold-down device immediately assumes its top release position and the container is very quickly released. The upward movement of the hold-down device in the direction of its release position does not therefore have to be brought about by the sampling unit, a simple spring is used instead for this purpose.

The interaction according to the invention between the sampling unit and the hold-down device demands but does not require that both components are movable along guides that are parallel to one another. In theory, both components can follow arbitrarily selectable movement curves in space as long as their desired interaction for the lowering of the hold-down device or the removing of the self-locking effect is obtained. Being able to move the sampling unit and the hold-down device with respect to one another in parallel, however, is to be selected as it is particularly advantageous because it is structurally simple and saves space.

The clamping element of the self-holding mechanism according to the invention can be in an arbitrary form which is familiar to the expert for interaction with the clamping body. For example, a cam disk is possible as a clamping element. Said cam disk, when developed in an in expedient manner, has the advantageous characteristic of being able to compensate for small changes in distance between the cam disk and the clamping body without the operation of the self-holding mechanism being impaired. To this end, the cam disk comprises a contour with a changing radius to its pivot center, a friction angle, which follows from the friction pairing, being produced in the respectively adjusting contact point between the contour and the clamping body, for which the resultant clamping force is always within said angle in order, as a result, to ensure the self-locking effect. Obviously other self-locking mechanisms which are familiar to the expert can be used according to the invention (toggle mechanism, freewheel etc.). Actively generated deformation of the clamping element, as a result of which the interaction with the clamping body can suddenly be eliminated, would also be conceivable for removing the self-locking effect.

A particularly expedient embodiment of the invention provides that the hold-down device is movable in the freewheel direction from the release position into the fixing position along a guide rod which is fixed in position and serves as a clamping body. An edge portion, which is connected to the hold-down device, slides along the guide rod and acts as a clamping element, tilts with the guide rod when the hold-down device and consequently the clamping element is to be moved upward in the opposite (blocking) direction toward the release position. The edge plate is coupled with the hold-down device so as to be pivotable by a small amount. In a first pivot position of the edge plate, which is preferably spring-preloaded and consequently permanently under tension, according to the invention self-locking occurs between the edge plate and the guide rod. If, on the other hand, the edge plate is moved into a second pivot position, which can be effected, for example, by the entrainment means or a separate actuator, the self-locking is thus eliminated, the edge plate in said new pivot position is able to be moved freely up and down along the guide rod such that the hold-down device is movable upward along the guide rod in the direction of the release position.

A further embodiment of the invention provides that the clamping element and the clamping body can be coupled together in a positive-locking manner for transmitting the clamping force. Whereas self-locking can also be formed exclusively as a result of a frictional connection, in addition to this or as an alternative to it, it is also possible between the clamping element and the clamping body to build up a positive locking connection which is to serve for transmitting the desired clamping force. To this end, it would be conceivable, for example, to provide along a guide rod, which is realized as a clamping body, sawtooth-like projections down which a small plate, which is realized as a clamping element, is able to slide step-by-step as long as the self-holding mechanism is moved in the freewheel direction. If, on the other hand, movement is to be generated in the opposite direction, the small plate is pressed from below against a sawtooth and consequently blocks further relative movement. The self-locking effect created in this manner can be eliminated as a result of temporarily pivoting or otherwise decoupling the small plate from the effective region of the guide rod, different mechanisms being familiar to the expert for this purpose. The advantage of positive-locking self-locking compared to self-locking based purely on friction is that the maintaining of certain frictional conditions is not absolutely necessary, and lubricant that inadvertently passes into the self-holding mechanism does not impair the operation of the self-holding mechanism. On the other hand, self-locking which is generated in a positive-locking manner is somewhat more expensive structurally. Obviously, it is also possible to combine positive locking and friction locking to generate the self-locking effect, which brings about a particularly reliable self-locking effect.

The first and second end position of the sampling unit are preferably arranged one above the other along a vertical path of movement, at the bottom end of which (second or bottom end position) the penetrating element has penetrated (from above) into the container. However, movement to the side or from down to up is also conceivable in order to penetrate into the container. Consequently, the first end position is located preferably, but not compulsorily, vertically above the second end position. Other positions of the end positions in space are also possible depending on access to the container. Likewise, the above-mentioned directional information such as "above", "below", "down" etc. are always to be understood with reference to a container that is penetrated from above. For other cases with containers that are penetrated at the side or from below, the spatial references are to be correspondingly adapted within the meaning of the invention.

BRIEF DESCRIPTION OF THE DRAWINGS

An embodiment of the invention is to be explained in more detail below by way of figures.

DETAILED DESCRIPTION OF EMBODIMENTS

Figure 1:
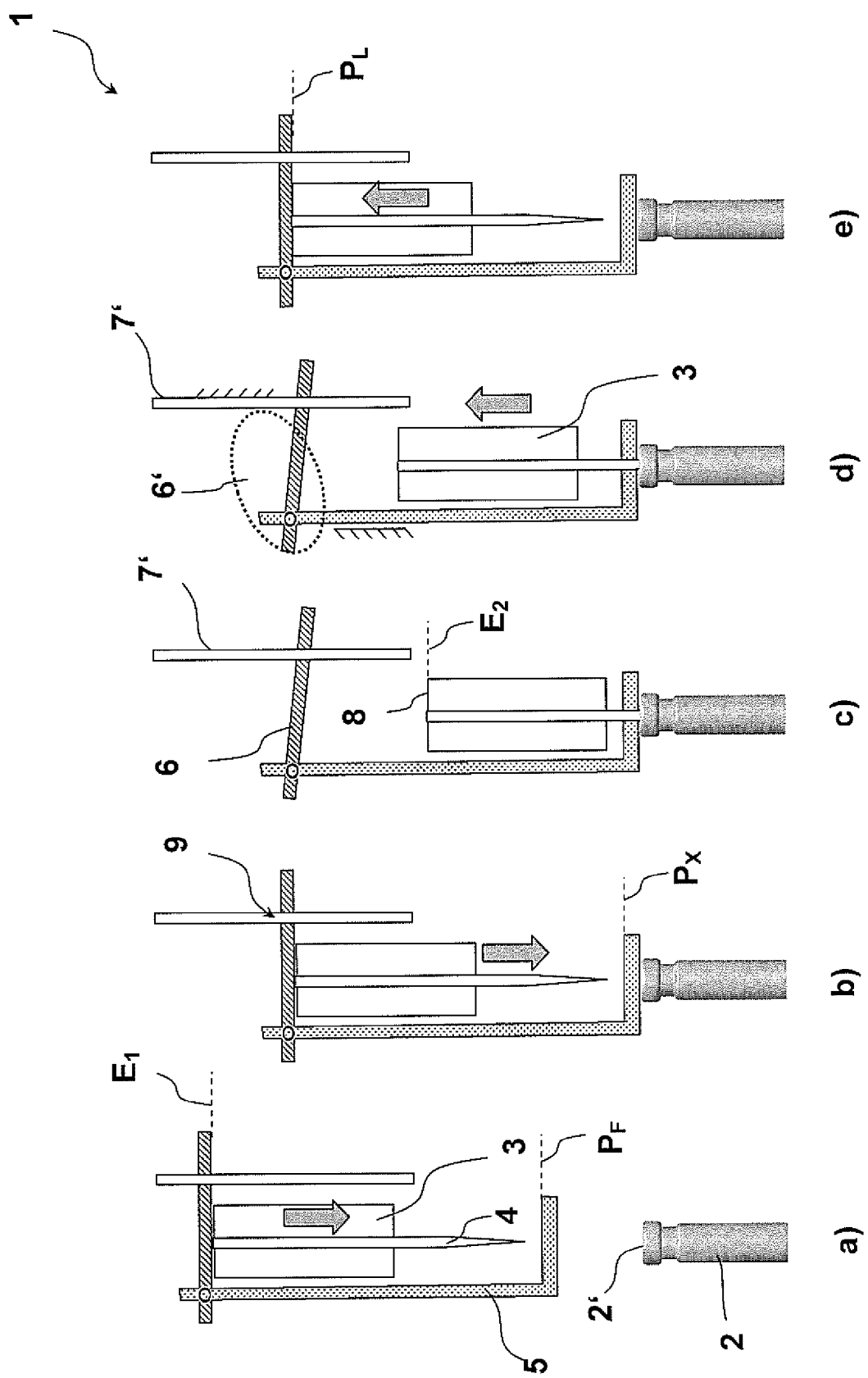
FIG. 1 shows a schematic representation of the operating principle.

FIG. 1 shows a schematic representation of the operating principle of the sample-taking unit 1 according to the invention. FIGS. 1a)-e), in this case, show the sequence of the essential steps of an operation for taking a sample from a container 2. FIG. 1a)-e) show in each case a vertically movable sampling unit 3, which at its bottom end carries a penetrating element which is realized as a sample needle or hollow needle 4 in order to be able to penetrate through a covering 2' (septum) on the surface of the container 2. The sampling unit 3, in this case, can be lowered from a first, in this case top end position $E_1$ to a second, in this case bottom end position $E_2$, which is shown in FIG. 1 c) in which the hollow needle 4 reaches down to a sufficient depth into the container 2 (the variant of a penetrating element that is realized as a pricker is not shown here—the sample needle is in direct contact with the septum in the bottom end position).

An L-shaped hold-down device 5 can also be moved in the vertical direction from a top release position $P_F$ into a bottom fixing position $P_X$, in which the hold-down device 5 rests on the container 2 or the septum 2' and as a result can prevent a vertical movement of the container upward. Pivotally mounted at the top end of the hold-down device 5 is a clamping element 6 which, in the form of an edge plate with a gap 9 realized therein, engages around a vertical guide rail 7 which is fixed in position as a clamping body 7 with a small amount of play (the gap 9 is slightly wider than the rail). The clamping element 6 and the guide rail 7 together form a self-holding mechanism which is able to keep the hold-down device 5 in its fixing position $P_X$.

The self-holding mechanism according to the invention is used in the following manner.

According to FIG. 1a) the sampling unit 3 is moved downward from its first (top) end position $E_1$. The sampling unit 3, in this case, carries the hold-down device 5 which is moved downward together with the sampling unit 3 until the latter has assumed its fixing position $P_X$ and fixes the container 2 according to FIG. 1b). During said downward movement of the hold-down device 5, the clamping element 6 slides downward along the guide rail 7' without resistance or in the freewheel direction as the gap 9 of the clamping element is able to be moved downward in a straight manner and consequently at a sufficient width along the guide rail 7'.

Once the fixing position $P_X$ has been achieved by the hold-down device, the sampling unit 3 is lowered further downward until it reaches its second (bottom) end position $E_2$ and by way of the hollow needle 4 extends down to a sufficient depth into the container 2, which is shown in FIG. 1 c). As a result of releasing the top surface of the sampling unit 3 from the bottom surface of the clamping element 6, the latter, on account of its own weight pivots downward clockwise due to gravity by a small amount about its pivot point at the top end of the leg of the hold-down device 5 until the edges of the gap 9 act upon both sides of the guide rail 7'. In the case of a subsequent upward movement of the sampling unit 3 shown in FIG. 1d) once the sample has been taken, via the pulled-up needle 4 and the septum 2' rubbing against it a vertical lifting force is exerted on the hold-down device 5, which, due to said force, strives to move upward. As a result of the tilting of the clamping element 6 with the rail, said movement however is blocked and on account of the self-locking effect which occurs between the clamping element 6 and the rail even an increased lifting force acting on the hold-down device 5 is unable to remove said clamping—the hold-down device 5 remains fixed in the fixing position $P_X$ whilst the sampling unit 3 with the needle 4 is able to be raised completely from the container, as is shown in FIG. 1e).

On its path upward the sampling unit 3 reaches the detaching position $P_L$. An entrainment means 8, which acts on the top surface of the sampling unit 3, in this case reaches the clamping element 6 from below and acts upon said clamping element with a detaching force which ultimately overcomes the existing clamping force and moves the clamping element 6 back into its horizontal alignment and, as a result, pivots the edges of the gap 9 out of their clamping position by the rail. As a result, the clamping function between the clamping element 6 and the rail which is fixed in position is removed such that the sampling unit 3, when continuing to move upward in the direction of the first (top) end position $E_1$, is also able to raise the hold-down device 5 until it reaches its release position $P_F$, as already shown in FIG. 1a).

FIG. 1d) shows a cam disk 6' as a possible alternative clamping element which fulfills a similar purpose as an edge plate which engages around the rail. Similar to the clamping element 6, it is pivotally mounted on the proud leg of the hold-down device 5 so as to be pivotable. Given the assumption that the rail 7 and the hold-down device 5 are secured against moving apart horizontally, the cam disk 6' is wedged against the rail 7', which is fixed in position, when the hold-down device 5 attempts to move upward in FIG. 1d) and blocks the hold-down device 5 in its fixing position $P_X$. Only the upwardly-moved sampling unit 3, which releases the cam disk 6' from the clamping from below, then also allows the hold-down device 5 to be raised again. This can be effected as a result of continuing contact between the top surface of the sampling unit 3 and the cam disk 6' or by means of further stop means that are not shown here whilst the sampling unit is moved upward.

Figure 2A:
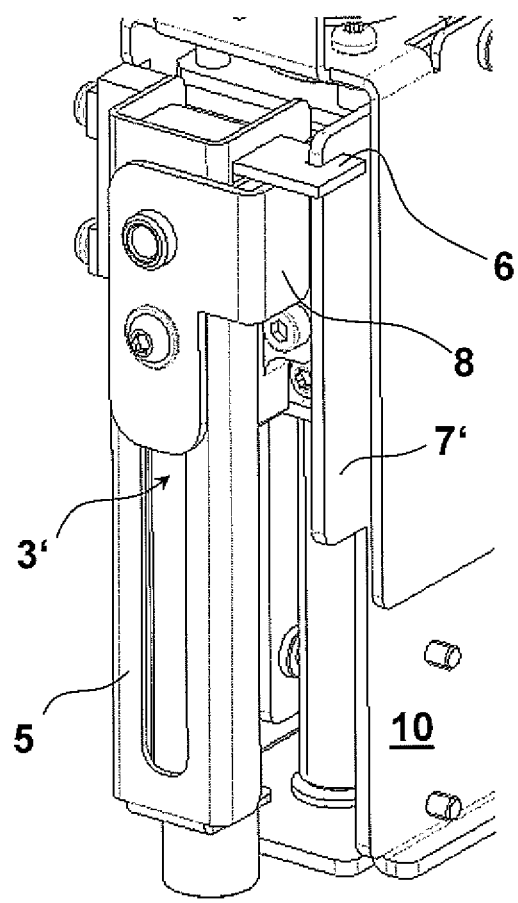
FIG. 2*a* shows a perspective view of a sample-taking unit that includes a hold-down device.

FIG. 2 shows a perspective view of details of an embodiment of the sample-taking unit according to the invention. In FIG. 2a) the hold-down device 5 can be moved downward along a guide (not identified in any more detail) relative to a chassis 10 which is fixed in position. A sampling unit 3', which is substantially concealed by the hold-down device 5, is also movable downward relative to the chassis 10 and parallel to the hold-down device 5. An entrainment means 8, which is moved up and down correspondingly with the sampling unit 3', is arranged on the sampling unit 3'.

Figure 2B:
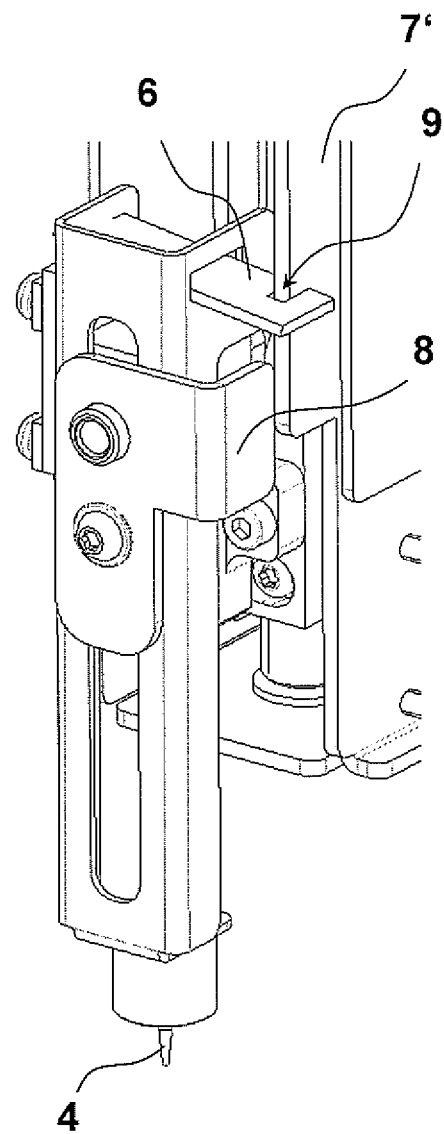
FIG. 2*b* shows a perspective view of the sample-taking unit in a completely lowered position with the sampling unit moved further down.

FIG. 2b) shows the hold-down device 5 in the completely lowered position, whilst the sampling unit 3' is moved further downward together with the entrainment means 8 in order to penetrate into the container (not shown) by way of the hollow needle 4. In this case, the entrainment means 8 is lowered further downward relative to the hold-down device 5 and at the same time on its top surface releases the contact with a clamping element 6 which is arranged as an edge plate on the hold-down device 5 so as to be pivotable by a small amount. The edge plate engages by way of a gap 9 around a rail 7' which is arranged fixed in position on the chassis 10 and tilts with said rail when the edge plate 6 and the rail 7' leave their alignment at right angles to one another. Said state has already been reached in FIG. 2b). An upward movement of the hold-down device 5 is prevented by the self-holding mechanism which is formed by the edge plate 6 and the rail 7', whilst the sampling unit 3' is able to move upward together with the entrainment means 8. In this case, the entrainment means 8 arrives from below against the edge plate 6 and aligns it at a right angle relative to the rail 7 again such that as a result the self-locking effect is removed and the hold-down device 5 is then also able to be raised upward together with the sampling unit 3'.

What is claimed is:

1. A sample-taking unit for taking samples from a container, the sample-taking unit comprising:
   a) a sampling unit including a top and a penetrating element, wherein the sampling unit is configured to be moved from a second end position into a first end position, in which the penetrating element projects into the container in the second end position, in which the penetrating element does not project into the container in the first end position, and
   b) a hold-down device configured to be moved relative to the penetrating element, wherein the hold-down device is also configured to
      b1) be moved from a fixing position into a release position, in which the hold-down device fixes the container in the fixing position, in which the hold-down device does not act upon the container in the release position, and
      b2) maintain the fixing position using a holding mechanism whilst the sampling unit is moved from the second end position in a direction of the first end position,
   c) in which the holding mechanism is a self-holding mechanism where the hold-down device is fixed in the fixing position as a result of a self-locking effect with a clamping force, the self-holding mechanism including a clamping element and a clamping body between which the self-locking effect is active,
   in that the self-locking effect is removable as a result of acting upon the clamping element which fixes the hold-down device with a detaching force, and
   as a result of moving the sampling unit relative to the hold-down device into a detaching position, where the top of the sampling unit or a protrusion of the sampling unit exerts the detaching force onto the clamping element.

2. The sample-taking unit of claim 1, in that the clamping body comprises a clamping rail.

3. The sample-taking unit of claim 1, in that a spring force is configured to bias the clamping element and/or a weight of the clamping element is configured to maintain a preloaded contact with the clamping body in order to bring about an immediate self-locking effect without play between the clamping element and the clamping body when a relative movement between the hold-down device and the clamping body is reversed.

4. The sample-taking unit of claim 3, in that the clamping body comprises a clamping rail.

5. The sample-taking unit of claim 1, in that the hold-down device is configured to be moved from the release position into the fixing position and back by a movement of the sampling unit.

6. The sample-taking unit of claim 1, in that the sampling unit and the hold-down device are configured to be moved along guides which are parallel to one another.

7. The sample-taking unit of claim 1, in that the clamping element includes a cam disk.

8. The sample-taking unit of claim 1, in that the clamping body includes a guide rod with a fixed position, in that the hold-down device is configured to be moved in a blockage-free manner from the release position into the fixing position along the guide rod, whilst the clamping element, which is connected to the hold-down device, is configured to slide along the guide rod and block a backward movement of the hold-down device in the direction of the release position as a result of a tilting with the guide rod as long as the clamping element does not experience any detaching force which eliminates the tilting.

9. The sample-taking unit of claim 1, in that the clamping element comprises an edge plate, in that the clamping body includes a guide rod, the edge plate being pivotably coupled to the hold-down device, the edge plate having a first pivot position where the edge plate and the guide rod are self-locked, the edge plate also having a second pivot position, in which the second pivot position is generated by the sampling unit or an actuator, where the edge plate and the guide rod are not self-locked where the hold-down device is movable along the guide rod in a direction of the release position.

10. The sample-taking unit of claim 1, in that the clamping element and the clamping body are configured to be coupled together in a positive locking manner to transmit the clamping force.

11. A sample-taking unit for taking samples from a container, the sample-taking unit comprising:
    a) a sampling unit including a top and a penetrating element, wherein the sampling unit is configured to be moved from a second end position into a first end position, in which the penetrating element projects into the container in the second end position, in which the penetrating element does not project into the container in the first end position, and
    b) a hold-down device configured to be moved relative to the penetrating element, wherein the hold-down device is also configured to
       b1) be moved from a fixing position into a release position, in which the hold-down device fixes the container in the fixing position, in which the hold-down device does not act upon the container in the release position, and
       b2) maintain the fixing position using a holding mechanism whilst the sampling unit is moved from the second end position in a direction of the first end position,
    c) in which the holding mechanism is a self-holding mechanism where the hold-down device is fixed in the fixing position as a result of a self-locking effect with a clamping force,
    in that the hold-down device is configured to be moved into the fixing position against a spring force which moves the hold-down device back into the release position when the self-locking effect is removed.

12. The sample-taking unit of claim 11, in that the self-holding mechanism comprises a clamping element and a clamping body between which the self-locking effect is active.

13. The sample-taking unit of claim 12, in that the clamping body comprises a clamping rail.

14. The sample-taking unit of claim 13, in that a spring force is configured to bias the clamping element and/or a weight of the clamping element is configured to maintain a preloaded contact with the clamping rail in order to bring about an immediate self-locking effect without play between the clamping element and the clamping body when a relative movement between the hold-down device and the clamping rail is reversed.

15. The sample-taking unit of claim 12, in that the clamping body has a fixed position and the clamping element is configured to be moved together with the hold-down device, or the clamping element has a fixed position and the clamping body is configured to be moved together with the hold-down device.

16. The sample-taking unit of claim 12, in that the self-locking effect is removable as a result of acting upon the clamping element which fixes the hold-down device with a detaching force,
  a) as a result of moving the sampling unit relative to the hold-down device into a detaching position, where the top of the sampling unit or a protrusion of the sampling unit exerts the detaching force onto the clamping element, or
  b) by an actuatable actuator which exerts the detaching force onto the clamping element.

17. The sample-taking unit of claim 12, in that the clamping body includes a guide rod with a fixed position, in that the hold-down device is configured to be moved in a blockage-free manner from the release position into the fixing position along the guide rod, whilst the clamping element, which is connected to the hold-down device, is configured to slide along the guide rod and block a backward movement of the hold-down device in the direction of the release position as a result of a tilting with the guide rod as long as the clamping element does not experience any detaching force which eliminates the tilting.

18. The sample-taking unit of claim 12, in that the clamping element comprises an edge plate, in that the clamping body includes a guide rod, the edge plate being pivotably coupled to the hold-down device, the edge plate having a first pivot position where the edge plate and the guide rod are self-locked, the edge plate also having a second pivot position, in which the second pivot position is generated by the sampling unit or an actuator, where the edge plate and the guide rod are not self-locked where the hold-down device is movable along the guide rod in a direction of the release position.

19. The sample-taking unit of claim 11, in that the hold-down device is configured to be moved from the release position into the fixing position and back by a movement of the sampling unit.

20. The sample-taking unit of claim 11, in that the sampling unit and the hold-down device are configured to be moved along guides which are parallel to one another.

21. The sample-taking unit of claim 11, in that the clamping element includes a cam disk.

* * * * *